United States Patent
Schwager

(10) Patent No.: US 9,625,069 B2
(45) Date of Patent: Apr. 18, 2017

(54) METHOD FOR CONNECTING PLASTIC TUBES BY PLASTICALLY DEFORMING AND WIDENING CONNECTING STUB

(75) Inventor: Michael Schwager, Winterthur (CH)

(73) Assignee: SIS MEDICAL AG, Frauenfeld (CH)

( * ) Notice: Subject to any disclaimer, the term of this patent is extended or adjusted under 35 U.S.C. 154(b) by 363 days.

(21) Appl. No.: 13/054,405

(22) PCT Filed: Jul. 8, 2009

(86) PCT No.: PCT/CH2009/000242
§ 371 (c)(1),
(2), (4) Date: Jan. 14, 2011

(87) PCT Pub. No.: WO2010/006456
PCT Pub. Date: Jan. 21, 2010

(65) Prior Publication Data
US 2011/0125134 A1 May 26, 2011

(30) Foreign Application Priority Data

Jul. 16, 2008 (CH) .................................... 1106/08

(51) Int. Cl.
*F16L 47/00* (2006.01)
*F16L 31/00* (2006.01)
(Continued)

(52) U.S. Cl.
CPC ............ *F16L 31/00* (2013.01); *A61L 24/046* (2013.01); *A61L 26/0019* (2013.01);
(Continued)

(58) Field of Classification Search
CPC ............ A61M 25/001; A61M 25/0013; A61M 25/0014; A61M 25/0015; A61M 25/0009; A61B 5/00
(Continued)

(56) References Cited

U.S. PATENT DOCUMENTS 3,035,113 A * 5/1962 Danchuk .................... 174/74 A
3,315,986 A    4/1967 Quick
(Continued)

FOREIGN PATENT DOCUMENTS

DE    200 04 312 U1    8/2000
EP    0 774 611 A1    5/1997
(Continued)

OTHER PUBLICATIONS

English translation of JP Office Action mailed Jul. 9, 2013 in Application No. 2011-517728.

*Primary Examiner* — Bhisma Mehta
*Assistant Examiner* — Matthew A Engel
(74) *Attorney, Agent, or Firm* — Birch, Stewart, Kolasch & Birch, LLP

(57) ABSTRACT

A method for coaxially connecting a first plastic tube (10, 110) to a second plastic tube (20, 120), said plastic tubes (10, 20) in particular being provided as part of a medical catheter (102), the two plastic tubes (10, 20) being connected by way of a tubular connecting piece (50), characterized in that the first plastic tube (10) and/or the second plastic tube (20) are integrally molded from the outside onto the tubular connecting piece (50) using a forming process such that an adhesive and/or positive connection is produced.

8 Claims, 3 Drawing Sheets

(51) Int. Cl.

| | |
|---|---|
| *A61M 25/00* | (2006.01) |
| *A61M 25/10* | (2013.01) |
| *A61L 24/04* | (2006.01) |
| *A61L 26/00* | (2006.01) |
| *A61L 27/18* | (2006.01) |
| *A61L 29/06* | (2006.01) |
| *A61L 31/06* | (2006.01) |
| *A61M 39/10* | (2006.01) |
| *A61M 39/14* | (2006.01) |

(52) U.S. Cl.
CPC ............... *A61L 27/18* (2013.01); *A61L 29/06* (2013.01); *A61L 31/06* (2013.01); *A61M 25/0009* (2013.01); *A61M 39/10* (2013.01); *F16L 47/005* (2013.01); *A61M 25/0014* (2013.01); *A61M 25/1029* (2013.01); *A61M 25/1036* (2013.01); *A61M 39/14* (2013.01)

(58) Field of Classification Search
USPC .... 156/158, 293–29, 307.34; 285/62, 381.4; 29/507; 604/533, 537; 403/27
See application file for complete search history.

(56) References Cited

U.S. PATENT DOCUMENTS

| | | | | |
|---|---|---|---|---|
| 3,957,382 | A * | 5/1976 | Greuel et al. ................... | 403/27 |
| 3,972,548 | A | 8/1976 | Roseen | |
| 4,092,193 | A * | 5/1978 | Brooks ........................... | 156/83 |
| 4,563,181 | A | 1/1986 | Wijayarathna et al. | |
| 4,636,272 | A * | 1/1987 | Riggs ............................. | 156/158 |
| 5,092,632 | A | 3/1992 | Washizu et al. | |
| 5,191,888 | A * | 3/1993 | Palmer et al. ................. | 600/434 |
| 5,549,949 | A | 8/1996 | Williams et al. | |
| 5,762,996 | A * | 6/1998 | Lucas et al. .................... | 427/2.3 |
| 7,549,975 | B2 * | 6/2009 | Lee et al. ................... | 604/96.01 |
| 8,403,885 | B2 * | 3/2013 | Arana et al. ................... | 604/103 |
| 8,840,743 | B2 * | 9/2014 | Wantink et al. ................ | 156/86 |
| 2001/0011066 | A1 * | 8/2001 | Ravi-Chandar ....... | H01L 39/248 505/430 |
| 2003/0018317 | A1 * | 1/2003 | Goebel ............. | A61M 25/0021 604/525 |
| 2005/0131445 | A1 * | 6/2005 | Holman et al. ................ | 606/194 |

FOREIGN PATENT DOCUMENTS

| | | | | |
|---|---|---|---|---|
| FR | 2 252 191 | A1 | 6/1975 | |
| JP | 50-85678 | | 7/1975 | |
| JP | 56-127878 | A | 10/1981 | |
| JP | 60-227090 | A | 11/1985 | |
| JP | 61-274197 | A | 12/1986 | |
| WO | WO 99/22170 | A1 | 5/1999 | |
| WO | WO 2007/140635 | A1 | 12/2007 | |
| WO | WO 2007140635 | A1 * | 12/2007 | ............. A61M 25/00 |
| WO | WO 2009055941 | A1 * | 5/2009 | ............. A61M 25/00 |
| WO | WO 2010006456 | A1 * | 1/2010 | ............. A61L 24/04 |

* cited by examiner

METHOD FOR CONNECTING PLASTIC TUBES BY PLASTICALLY DEFORMING AND WIDENING CONNECTING STUB

TECHNICAL FIELD

The invention relates to a method for coaxially connecting a first plastic tube to a second plastic tube, which plastic tubes are provided in particular as component parts of a medical catheter, the two plastic tubes being connected by way of a tubular connecting piece. Furthermore, the invention relates to use of the method in the production of a catheter and to an arrangement comprising two plastic tubes that are connected to one another.

PRIOR ART

Particularly in the production of medical catheters, it is necessary to connect plastic tubes with different material properties to one another in order to adapt different regions of the catheter optimally to the respective requirements. In order to ensure that a catheter can be inserted well, the tip region of the catheter is generally formed by a relatively flexible plastic tube, while the portions of the catheter lying behind said tip consist of more rigid plastic tubes.

The plastic tubes of different types are in this case usually adhesively bonded to one another and/or welded to one another.

However, welding of plastic tubes is generally only possible if the plastic tubes to be connected or their polymer materials are very similar with respect to the chemical structure. In U.S. Pat. No. 4,563,181, for example, a description is given of butt welding a catheter shaft made of nylon (polyamide) to a catheter tip made of a relatively soft polyether-polyamide copolymer compatible with nylon. However, such a method is based on compatible material combinations, which usually have to be determined in onerous development processes.

With the bonding of plastic tubes, although there is greater flexibility, the precise application of the adhesive, particular in the case of small diameters of the plastic tubes suitable for catheters, is likewise onerous.

Particularly for the production of medical catheters, therefore, there continues as before to be a need for a method which makes it possible for plastic tubes to be connected more easily and securely, even if they are made of chemically different materials.

SUMMARY OF THE INVENTION

The object of the invention is therefore to provide a method in the technical area mentioned at the beginning which can be used more flexibly and makes it possible for plastic tubes to be connected easily and at the same time securely, particularly in the production of medical catheters.

The way in which the object is achieved is defined by the features of claim 1. According to the invention, the first plastic tube and/or the second plastic tube are integrally molded from the outside onto the tubular connecting piece in a forming process, so that an adhesive and/or positive connection is formed.

In this context, a plastic tube is understood as meaning a thin tube made of a plastic, which preferably has a diameter of at most 3 mm, particularly preferably a diameter of at most 2 mm and most particularly preferably a diameter of at most 1 mm.

A wall thickness of the plastic tubes measures particularly at most 0.5 mm, particularly preferably at most 0.2 mm and most particularly preferably at most 0.1 mm.

The term forming process or forming relates in this context to a process in which a body, for example a plastic tube, is deliberately plastically deformed and brought into a new form, the volume and the mass of the formed body being maintained.

In principle, at least one of the two plastic tubes to be connected is connected to the tubular connecting piece by the forming process according to the invention. It is well within the scope of the invention that the other plastic tube is connected to the tubular connecting piece by a different connecting technique, for example by material bonding, if it is expedient to do so. The use of a first plastic tube which already has a tubular connecting piece at one end or the formation of a tubular connecting piece in an end region of the first plastic tube is also possible.

During the forming process, an actual plastic deformation of the first and/or the second plastic tube occurs. The forming process has the effect that the boundary surface layers of the inner regions of the first and/or the second plastic tube are brought into direct contact with the boundary surface layer of the outer region of the tubular connecting piece. Since, during the forming process, the plastic tubes are integrally molded onto the tubular connecting piece or onto the outer contour thereof, the contact surface areas of the boundary surface layers of the plastic tubes and the boundary surface layers of the tubular connecting piece are maximized. As a result, an adhesive connection or mechanical cohesion between the plastic tubes and the tubular connecting piece is obtained, based in particular on interlocking bonds on a microscopic scale and/or atomic and/or molecular interactions between the boundary surface layers of the plastic tubes and the tubular connecting piece.

Adhesive connections of this type are in particular also fluid-tight, making it possible to dispense with the sealing of the connection by additional sealing compounds, for example adhesives. This is of advantage particularly in the case of medical catheters.

Depending on the configuration of the outer region of the tubular connecting piece, a positive connection on a microscopic scale can also be formed during the forming process, which, in addition to the adhesive connection, increases the mechanical stability of the connection between the plastic tubes and the tubular connecting piece.

The forming process according to the invention allows adhesive-free and mechanically stable connections to be formed between the plastic tubes and the tubular connecting piece. This is of great advantage particularly in the case of plastic tubes that have a diameter of at most 3 mm. For example, the uniform and precise application of adhesive is relatively onerous in practice in the case of such thin plastic tubes. Moreover, there is the risk of the adhesive inadvertently getting inside the plastic tube when it is being applied. The removal of this adhesive unwantedly introduced into the plastic tube is then correspondingly difficult and laborious. Accordingly, welding operations also have to be carried out very precisely on such thin plastic tubes, for one reason because of the small wall thicknesses, in order that the plastic tubes are not damaged. Moreover, the welding of plastic imposes certain requirements on the materials used, since not all plastics can be welded to one another. The welding of plastic to other materials, such as for example metal, is also not possible, which restricts the choice of materials for the tubular connecting piece, which does not necessarily have to consist of plastic.

Since the plastic tubes are integrally molded onto the tubular connecting element from the outside, the tubular connecting element may in particular be encased or enclosed completely by the plastic tubes. In this way, any edges and/or projections of the tubular connecting piece are covered by the plastic tubes. Edge regions of the plastic tubes themselves may, for example, be formed during the forming process according to the invention in particular in such a way that they are rounded-off and/or beveled. This may be of great advantage, for example in the case of catheters, since they must be guided through sensitive and sometimes narrow hollow organs of the human and/or animal body. Projections or edges of the connected joint would damage or injure the hollow organs.

It has been found that the connections that can be produced according to the invention have great mechanical stability and are also extremely stable, in particular with respect to tensile loads.

Consequently, the method according to the invention offers significant advantages, in particular over the welding and/or adhesive bonding of plastic tubes, and can moreover be used flexibly, even with different materials. Since the method according to the invention is advantageous specifically in the case of very thin plastic tubes, it is particularly suitable for the production of medical catheters.

The first plastic tube and/or the second plastic tube are preferably softened during the forming process by a heat treatment and are integrally molded onto the tubular connecting piece by a pressing force acting in a radial direction. The heat treatment has the effect that the boundary layer of the first and/or the second plastic tube softens, whereby the integral molding onto the tubular connecting piece is made easier. The pressing force that acts on the first and/or the second plastic tube particularly during the heat treatment allows the tube to be integrally molded onto the outer contour of the tubular connecting piece in the best way possible, since the plastic tube is in this case in the softened state. In this way, greatest possible adhesion between the plastic tubes and the tubular connecting piece is produced.

The pressing force advantageously acts on the plastic tube in all radial directions, so that the plastic tube is pressed onto the tubular connecting piece uniformly from all directions.

A shrink-fit tube, which consists, for example, of a plastic such as for example polyolefins, polyvinyl chloride or Teflon, is particularly suitable for carrying out the forming process. The shrink-fit tube can be pushed directly over the regions of the plastic tubes that are to be integrally molded onto the tubular connecting piece during the forming process. By supplying heat, for example in the form of hot air and/or electromagnetic radiation, the shrink-fit tube can be heated up, so that it contracts to a great extent in the radial direction and a pressing force acts on the plastic tubes. The heat supplied at the same time allows the plastic tubes to be softened and/or incipiently melted. The shrink-fit tube can be removed again after the forming process or else left on the connected plastic tubes. In the latter case, the shrink-fit tube can serve as additional stabilization and/or as protection from the connected joint.

In principle, however, it is within the scope of the invention to allow a pressing force to act for the forming during the forming process, if it is possible on the basis of the material properties of the plastic tube. However, this is at the expense of best-possible adhesion between the plastic tubes and the tubular connecting piece.

In particular, before the forming process, an end region of the first plastic tube is pushed coaxially over a first end of the tubular connecting piece and an end region of the second plastic tube is pushed coaxially over a second end of the tubular connecting piece. The tubular connecting piece is in this case in the form of a separate hollow cylinder or a short piece of tube. This allows the two plastic tubes that are to be connected to be arranged in the intended position already before the forming process. The forming process can, for example, be subsequently carried out simultaneously for both plastic tubes, which in particular saves time.

However, it is also conceivable to connect the end region of the first plastic tube to the first end of the tubular connecting piece in a first step and only then connect the end region of the second plastic tube to the second end of the tubular connecting piece.

In principle, it is also possible to connect a first plastic tube that is fitted with a further inner tube protruding from the first plastic tube to the second plastic tube. For this purpose, the tubular connecting piece has in particular an inside diameter which is at least as great as the outside diameter of the inner tube of the first plastic tube. The tubular connecting piece can in this case be pushed onto the inner tube and the first end of the tubular connecting piece can then be introduced into the end region of the first plastic tube. After that, the second plastic tube can be pushed first over the inner tube protruding from the first plastic tube and then over the second end of the tubular connecting piece.

A modulus of elasticity of the tubular connecting piece greater than a modulus of elasticity of the first plastic tube and greater than a modulus of elasticity of the second plastic tube is preferred. Such an arrangement is more stable, in particular with respect to tensile loads. This is so because, under tensile loading, the plastic tubes have a tendency to contract in diameter. This produces a force in a radial direction that acts on the tubular connecting piece. The greater the modulus of elasticity of the tubular connecting piece, the better it can withstand the force acting in the radial direction without itself being deformed to a great extent. In this way, under tensile loading, a non-positive connection is additionally produced between the plastic tubes and the tubular connecting piece, increasing the mechanical strength of the connection.

In principle, it is also possible to provide a tubular connecting piece with a lower modulus of elasticity. This may be advantageous under some circumstances in order to increase the flexibility of the connected joint. However, in this case the advantage of the additional non-positive connection between the tubular connecting piece and the plastic tubes is foregone.

The first plastic tube used preferably consists of a first thermoplastic material, for example of polyethylene terephthalate, and the second plastic tube preferably consists of a second thermoplastic material, for example of nylon. Heat treatment can be used without any problem on such thermoplastic materials to make them soften or begin melting and undergo forming in the softened state. Since the softening or incipient melting of the thermoplastic material is reversible, the material properties of the plastic tubes are not changed and/or impaired by the forming process.

Arrangements of plastic tubes made of such thermoplastic materials are particularly suitable for medical catheters. In this case, for example, a plastic tube of polyethylene terephthalate can be arranged as a catheter shaft and a plastic tube of nylon can be arranged in the region of the catheter tip. Since plastic tubes made of polyethylene terephthalate and of the same dimensions are generally more rigid than plastic tubes made of nylon, catheters formed in this way can be introduced well into the hollow organs.

In principle, however, it is also conceivable to use plastic tubes made of other plastics that can undergo forming.

It may also be advantageous additionally to push the end region of the first plastic tube coaxially over the end region of the second plastic tube before the forming process. The end region of the first plastic tube is in this case at least partially integrally molded onto the end region of the second plastic tube during the forming process. It is in this way possible in particular to prevent a gap from being formed between the two plastic tubes to be connected, whereby the tightness of the connection between the two plastic tubes is improved. However, it is also possible to push the two plastic tubes to be connected with their end faces against one another. Although under some circumstances the connection between the two plastic tubes is then less tight, there is the advantage that the overall diameter of the connected joint is thinner.

In this case, a modulus of elasticity of the first plastic tube is preferably greater than a modulus of elasticity of the second plastic tube. This particularly improves the mechanical strength of the direct connection between the two plastic tubes. Since the first plastic tube, which is arranged within the end region of the second plastic tube, contracts to a lesser extent under tensile loading than the second plastic tube lying over it, a non-positive connection directly between the first plastic tube and the second plastic tube is additionally produced under tensile loading.

However, it is also possible to use a first plastic tube with a modulus of elasticity which is lower than the modulus of elasticity of the second plastic tube. In this case, however, the improvement in the mechanical strength under tensile loading is foregone.

In particular, the tubular connecting piece that is used consists of polyimide. Polyimide has proven to be advantageous as a material for the tubular connecting piece, since polyimide has a relatively great modulus of elasticity and consequently is difficult to deform. At the same time, however, there is a certain flexibility, which is desirable particularly in the case of the connection of flexible plastic tubes. Furthermore, the shrinkage of polyimide under the effect of heat is extremely low in the temperature range of interest here. A tubular connecting piece made of polyimide therefore remains extremely stable in shape even at the temperatures prevailing during the forming process.

In principle, instead of a tubular connecting piece made of polyimide, a connecting piece made of steel or some other material that is difficult to deform and shrinks as little as possible under the effect of heat may also be used.

In particular, a wall of the tubular connecting piece is reinforced with an embedded wire coil. During the forming process, the wall of the tubular connecting piece, which consists, for example, of a thermoplastic material, may be integrally molded onto the embedded wire coil. As a result, a helical structure is formed on the outer side of the tubular connecting piece. The first and/or the second plastic tube are in this case integrally molded onto the helical structure during the forming process, whereby a positive connection is formed between the plastic tube and the tubular connecting piece. This improves the mechanical strength of the connection or the arrangement of the plastic tubes and the tubular connecting piece.

However, it is also possible to dispense with an embedded wire coil and/or to use tubular connecting pieces with structured outer sides.

In a preferred variant, the tubular connecting piece therefore has a structured outer lateral surface. The structured outer lateral surface may, for example, comprise projections and/or grooves and/or screw threads and/or peripheral flanges. Since the plastic tubes are integrally molded onto the structured outer lateral surface of the tubular connecting piece during the forming process, a positive connection between the plastic tubes and the tubular connecting piece is formed, improving the mechanical strength.

However, it is also possible to use tubular connecting pieces without structured outer sides or lateral surfaces. However, in this case the mechanical strength of the connection is reduced in comparison with a structured outer lateral surface.

In a further advantageous variant, a helical spring is used as the tubular connecting piece, the helical spring consisting in particular of metallic wire. Helical springs have proven to be advantageous as tubular connecting pieces, since, although they have relatively great bending flexibility with respect to the longitudinal axis, they are at the same time only a little flexible in the radial direction. Moreover, helical springs have a structured outer lateral surface on account of the turns of wire arranged next to one another. Since the helical spring is only a little flexible in the radial direction, the plastic tubes can be integrally molded well onto the helical springs or the individual wire turns in the forming process. This allows a positive connection between the helical spring and the plastic tubes to be produced in a simple manner. Arrangements produced in this way, comprising plastic tubes that are connected by way of a helical spring, are distinguished by high mechanical strength, but are nevertheless relatively flexible with respect to a longitudinal direction.

Individual turns of the helical spring have a spacing which corresponds to 10-50% of a wire diameter of the helical spring. An arrangement comprising plastic tubes that are connected by way of a helical spring with individual turns spaced apart in this way is distinguished in particular by optimum flexibility in the region of the connected joint. In particular, the bending flexibility of the connected joint with respect to a longitudinal direction is optimized in this way.

However, it is also possible in principle to use a helical spring in which the individual turns of wire have a spacing of more than 50% of the wire diameter of the helical spring. In this case, however, there is the risk of the plastic tubes being pressed into the inner region of the helical spring during the forming process. Moreover, the bending flexibility with respect to the longitudinal axis is no longer significantly improved by the greater spacing. Smaller spacings of less than 10% of the wire diameter are also possible in principle. However, the bending flexibility then decreases correspondingly.

However, it is also possible to arrange individual turns of the helical spring abutting one another. This may be advantageous if, for example, the inner lateral surface of the helical spring is to be formed as uniformly as possible. In particular, if the arrangement produced comprising the plastic tubes connected by the helical spring is a component part of a guiding wire lumen of a medical catheter, this may be advantageous, since individual projecting turns of the helical spring that hinder the movement of the guiding wire are avoided.

If a separate tubular connecting piece is used, preferably both the first plastic tube and the second plastic tube are integrally molded onto the tubular connecting piece with a positive connection. A connection that is optimized with respect to mechanical strength is created in this way.

In principle, however, it is also within the scope of the invention to integrally mold only the first plastic tube or the second plastic tube onto the tubular connecting piece with a positive connection. In this case, the plastic tube that is not connected with a positive connection can, for example, be adhesively fastened. It is similarly within the scope of the invention to connect both plastic tubes to the tubular connecting piece without a positive connection, for example adhesively.

In a further advantageous embodiment, before the forming process, the first end region of the first plastic tube is formed into a connecting stub. In this case, the tubular connecting piece consists of an end region of the first plastic tube that is formed into a connecting stub, the connecting stub preferably having substantially a smaller outside diameter than the first plastic tube. The connecting stub in this case assumes the function of the tubular connecting piece. In this way it is possible to dispense with a separate tubular connecting piece. As mentioned above, the tubular connecting piece may, however, also take the form of a separate part.

In this case, a modulus of elasticity of the first plastic tube greater than a modulus of elasticity of the second plastic tube is preferred. Since the connecting stub is in this case formed from the first plastic tube, the connecting stub has a modulus of elasticity which is greater than the modulus of elasticity of the second plastic tube. In this way, a higher mechanical strength of the connection between the connecting stub and the second plastic tube is obtained. Under tensile loading, the second, outer-lying plastic tube contracts and presses in the radial direction onto the connecting stub. On account of the higher modulus of elasticity of the connecting stub, the latter contracts to a lesser extent than the second plastic tube. This results overall in an additional non-positive connection between the second plastic tube and the connecting stub.

In principle, the second plastic tube may also have a higher modulus of elasticity than the first plastic tube. However, there is in this case the risk of the connecting stub slipping out of the second plastic tube under tensile loading, since in this case the connecting stub contracts to a greater extent under tensile loading than the second plastic tube.

During the forming of the first plastic tube into the connecting stub, an outside diameter of the connecting stub is preferably formed such that it is substantially narrowed in comparison with the outside diameter of the first plastic tube. This allows the second plastic tube to be pushed over the connecting stub more easily thereafter. Furthermore, in this way the outside diameter of the connected joint can be minimized, which is of advantage particularly in the case of medical catheters.

However, it is also conceivable in principle to form the outside diameter of the connecting stub greater in comparison with the outside diameter of the first plastic tube. This may be advantageous, for example, in order additionally to produce a positive connection between the two plastic tubes.

To produce the connecting stub, preferably an end portion of a cylindrical piece of wire is inserted into the first end region of the first plastic tube and subsequently the first end region of the first plastic tube is integrally molded from the outside onto the end region of the cylindrical piece of wire by forming. The use of such a piece of wire makes it possible in particular to produce a connecting stub with a uniform wall thickness and a clearly defined inside diameter.

An outside diameter of the end portion of the cylindrical piece of wire in this case measures particularly 60-80%, particularly preferably 65-75%, of the inside diameter of the first plastic tube before the formation of the connecting stub. It has been found that, with pieces of wire dimensioned in this way, very good results can be achieved with most plastic tubes with respect to the quality of the connecting stubs. In particular, connecting stubs produced in this way have stabilities that are comparable with the stability of the plastic tubes as such. Moreover, it is ensured that the connecting stub has adequate through-flow and at the same time a significant narrowing can be achieved in comparison with the plastic tube before the formation of the connecting stub.

In particular, before the forming process, the second plastic tube is pushed coaxially over the connecting stub, at least over the entire length thereof. This ensures that a maximum contact area between the connecting stub and the second plastic tube is formed during the subsequent forming process, whereby, as already mentioned above, the adhesive connection or the mechanical cohesion is optimized.

However, it is also possible to push the second plastic tube further, so that it comes to lie beyond the connecting stub, over the first plastic tube. This is of advantage in particular whenever the connecting stub has a greater outside diameter than the first plastic tube, since then a positive connection can be additionally produced during the forming process.

However, an arrangement in which the second plastic tube is merely pushed partially over the connecting stub is also practicable. However, the shorter the common contact area between the second plastic tube and the connecting stub turns out to be, the smaller the adhesive connection.

It is particularly preferred for a free end of the connecting stub to be widened before the forming process. Making the free end wider than the other regions of the connecting stub makes it possible in the subsequent forming process to produce a positive connection, which in particular improves the mechanical cohesion between the connecting stub and the second plastic tube.

However, instead of or in addition to widening the free end, it is also possible in principle to widen another region of the connecting stub, for example a region lying behind the free end of the connecting stub. It is also possible to dispense with widening of the connecting stub entirely. However, this is at the expense of maximum cohesion between the connecting stub and the second plastic tube.

To widen the free end of the connecting stub, a thickened region of the cylindrical piece of wire that adjoins the end region of the cylindrical piece of wire and/or a widened transitional region with respect to the thickened region is advantageously pushed into the free end of the connecting stub in a direction toward the first plastic tube. The transition between the end portion of the cylindrical piece of wire and the thickened region of the cylindrical piece of wire is in this case formed in particular in such a way that it is conical and/or rounded-off, so that the thickened region of the cylindrical piece of wire is pushed as well as possible into the free end of the connecting stub.

However, it is also possible, for example, to use a conically tapering wire for the widening of the connecting stub and/or to widen the free end of the connecting piece by making it begin to melt.

An outside diameter of the thickened region of the cylindrical piece of wire preferably corresponds substantially to the inside diameter of the first plastic tube before the production of the connecting stub. It has been found that a piece of wire dimensioned in this way is particularly suitable for achieving widening of the connecting stub that is adequate for a positive connection without damaging the connecting stub during the widening.

Preferably, during the forming process, the second plastic tube is integrally molded onto the connecting stub widened at the end, thereby forming a positive connection. As a result, an extremely stable connection between the second plastic tube and the connecting stub or the first plastic tube connected to the latter is obtained.

Advantageously, during the forming process, the end portion of the cylindrical piece of wire remains in the connecting stub and the widened transitional region of the cylindrical piece of wire and/or the thickened region of the cylindrical piece of wire remains in the widened free end of the connecting stub. This allows a predetermined through-flow of the connected joint to be guaranteed, since the connecting stub cannot narrow any further during the forming process, even if a pressing force is applied or under the influence of heat. This is particularly decisive if the plastic tubes are intended, for example, for conducting fluid and/or as a guiding channel for a wire in the case of a catheter. Moreover, it is thereby guaranteed that the second plastic tube can be optimally integrally molded onto the connecting stub, since the connecting stub is supported on the inside. The thickened region of the cylindrical piece of wire in the widened end of the connecting stub guarantees in particular that the widened region does not narrow again during the forming process.

This makes the formation of a positive connection possible, the connecting stub still being in a widened state at the free end, in particular even after the forming process, and the second plastic tube being integrally molded onto the connecting stub in a positively connected manner.

However, it is also conceivable to remove the cylindrical piece of wire from the connecting stub before the forming process. However, the forming process must then be correspondingly monitored very closely, which under some circumstances is onerous.

In a further preferred variant, the first plastic tube and/or the second plastic tube are spirally wound up after the forming process and formed into a dimensionally stable spiral under the application of heat. The first plastic tube and/or the second plastic tube is therefore in the form of a dimensionally stable spiral after the application of heat. In this way, even relatively long plastic tubes can be packed and stored in a space-saving way, for example in a packaging sleeve. Since the wound-up spiral is dimensionally stable after the application of heat, it retains its spiral form even after removal of the packaging sleeve. Uncontrolled unrolling of the plastic tube is thus effectively prevented. However, it is also possible to dispense with spiral winding-up and/or the formation of a dimensionally stable spiral.

The method according to the invention thus allows in particular the production of arrangements that comprise a first plastic tube which is connected to a second plastic tube by way of a tubular connecting piece, the first plastic tube and/or the second plastic tube being integrally molded from the outside onto the tubular connecting piece and adhesively and/or positively connected to the connecting piece.

Such arrangements can be formed in particular with small outside diameters by the method according to the invention. Consequently, the arrangements according to the invention and the method according to the invention are particularly suitable for use in the production of medical catheters.

Further advantageous embodiments and combinations of features of the invention emerge from the following detailed description and from the patent claims in their entirety.

BRIEF DESCRIPTION OF THE DRAWINGS

In the drawings used to explain the exemplary embodiment.

In principle, the same parts are provided with the same designations in the figures.

Ways of Implementing the Invention

Figure 1A:
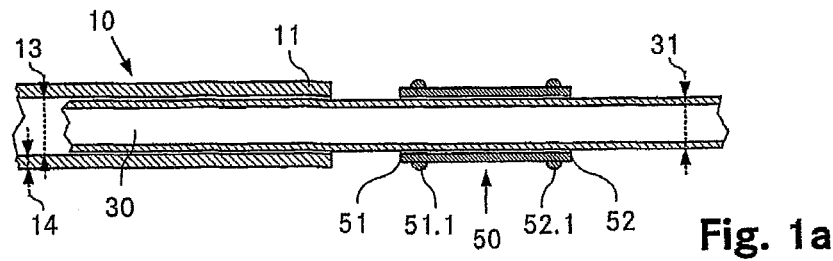
FIG. 1a shows a longitudinal section through a first plastic tube with an inner tube protruding from it, a tubular connecting piece having been pushed over the inner tube.
Figure 1B:
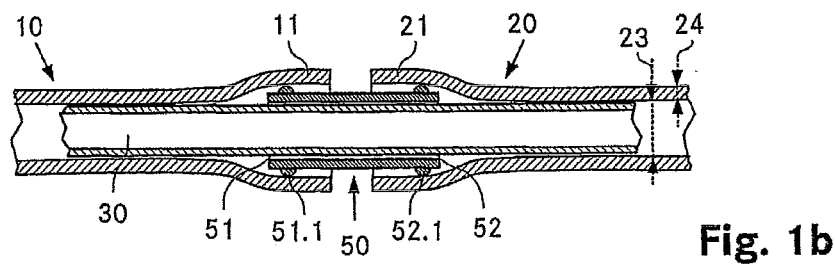
FIG. 1b shows a longitudinal section through the tubular connecting piece that has been pushed into an end region of a first plastic tube and an end region of a second plastic tube.
Figure 1C:
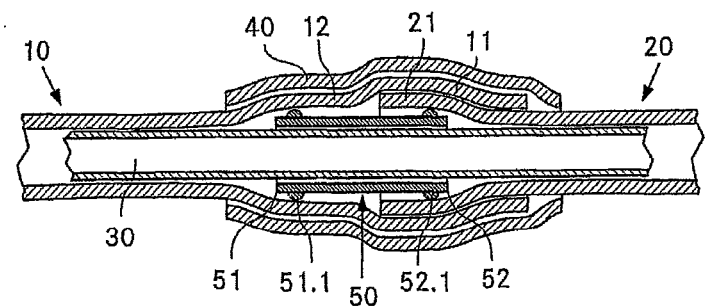
FIG. 1c shows a longitudinal section through the arrangement from FIG. 1b, the end region of the first plastic tube additionally having been pushed over the end region of the second plastic tube and surrounded by a shrink-fit tube.
Figure 1D:
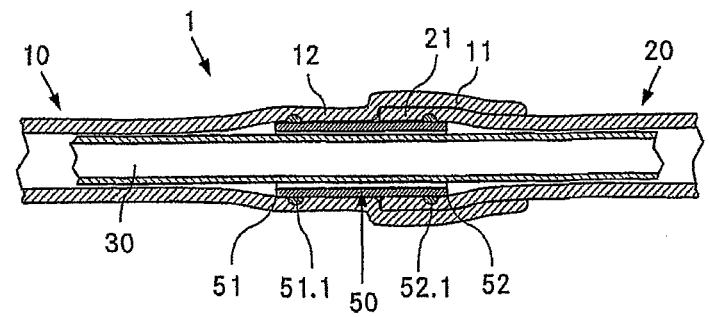
FIG. 1d shows a longitudinal section through the arrangement from FIG. 1c after the forming process and removal of the shrink-fit tube.

In FIGS. 1a-1c, various intermediate stages that are run through when a first method according to the invention is carried out are represented. FIG. 1d shows a first arrangement 1 that can be produced by the method according to the invention.

On the left-hand side in FIG. 1a, an end region 11 of the first plastic tube 10 is depicted in longitudinal section. The first plastic tube 10 is cylindrical and has an inside diameter 13 of, for example, 0.7 mm with a wall thickness 14 of, for example, 0.1 mm and consists of polyethylene terephthalate (PET). Arranged inside the first plastic tube 10 is a coaxial and cylindrical inner tube 30, which protrudes from the end region 11 of the first plastic tube 10. The outside diameter 31 of the inner tube 30 in this case corresponds approximately to the inside diameter 13 of the first plastic tube 10.

As a tubular connecting piece, a cylindrical polyimide tube 50 has been pushed coaxially over a region of the inner tube 30 protruding from the first polyimide tube 10. The inside diameter of the polyimide tube 50 corresponds approximately to the inside diameter 13 of the first plastic tube 10. In the region of the first end 51 of the polyimide tube 50 that is facing the first plastic tube 10, a first flange 51.1 protrudes from the outer lateral surface of the first plastic tube 10. The first flange 51.1 has a semicircular cross section and runs completely around the polyimide tube 50, which however cannot be seen in FIG. 1a. In the region of the second end 52 of the polyimide tube 50, a second flange 52.1 protrudes from the outer lateral surface of the polyimide tube 50. Like the first flange 51.1, the second flange 52.1 has a semicircular cross section and runs completely around the polyimide tube 50, which likewise cannot be seen in FIG. 1a.

FIG. 1b shows the situation after the first end 51 of the polyimide tube 50 has been pushed into the first plastic tube 10 and a second plastic tube 20 has been pushed onto the second end 52 of the polyimide tube 50.

In this case, the first end 51 of the polyimide tube 50 is in the end region 11 of the first plastic tube 10. The end region 11 of the first plastic tube 10 therefore completely surrounds the first end of the polyimide tube 50. In a longitudinal direction of the polyimide tube 50, the end region 11 of the first plastic tube 10 thereby protrudes beyond the first flange 51.1 of the polyimide tube 50. On account of the pushed-in polyimide tube 50, the end region 11 of the first plastic tube 10 is widened slightly in the radial direction.

Furthermore, an end region 21 of a second plastic tube has been pushed over the second end 52 of the polyimide tube 50. The second plastic tube 20 thereby protrudes coaxially in the longitudinal direction beyond the second flange 52 of the polyimide tube 50. The second plastic tube 20 is likewise cylindrical, consists, for example, of nylon and has an inside diameter 23 of, for example, 0.7 mm with a wall thickness 24 of, for example, 0.1 mm. The end region 21 of the second plastic tube 20 is likewise slightly widened in the radial direction on account of the pushed-in polyimide tube 50. The first plastic tube 10 and the second plastic tube 20 accordingly have the same dimensions with respect to their diameters 13, 23 and wall thicknesses 14, 24 and lie with their end faces coaxially opposite.

A modulus of elasticity of the polyimide tube 50 is in this case greater than a modulus of elasticity of the first plastic tube 10, while a modulus of elasticity of the second plastic tube 20 is less than the modulus of elasticity of the first plastic tube 10.

FIG. 1c shows the situation after the end region 11 of the first plastic tube 10 has been pushed in the longitudinal direction over the end region 21 of the second plastic tube 20. The first plastic tube 10 in this case protrudes in the longitudinal direction beyond the second end 52 of the polyimide tube 50 and beyond the widened end region 21 of the second plastic tube 20. The end region 11 of the first plastic tube 10 therefore completely surrounds the end region 21 of the second plastic tube 20 and in the overlapping region is additionally partially widened in the radial direction. A rear region 12, adjoining the end region 11, of the first plastic tube 10 also surrounds the region of the polyimide tube 50 that is not surrounded by the second plastic tube 20.

Loosely arranged around the end region 11 and around the rear region 12 of the first plastic tube 10 is a shrink-fit tube 40. The shrink-fit tube 40 completely surrounds the widened regions of the two plastic tubes 10, 20.

The arrangement represented in FIG. 1c corresponds to the starting situation directly before the forming process.

In FIG. 1d, a first arrangement 1 according to the invention, comprising the two plastic tubes 10, 20 and the polyimide tube 50, is represented after the forming process. The shrink-fit tube 40 represented in FIG. 1c has been removed again after the forming process.

On account of the forming process, the end region 21 of the second plastic tube 20 has been integrally molded onto the region of the second end 52 of the polyimide tube 50 and adhesively connected to it. Since the end region 21 of the second plastic tube 20 has also been integrally molded onto the second flange 52.1, there is also a positive connection between the end region 21 of the second plastic tube 20 and the polyimide tube 50.

The end region 11 of the first plastic tube 10 has been integrally molded from the outside onto the end region of the second plastic tube 20 and adhesively connected to it. The rear region 12 of the first plastic tube 10 has been integrally molded onto the first end 51 of the polyimide tube 50 and in this way also onto the first flange 51.1, whereby there is an adhesive and positive connection between the first plastic tube 10 and the polyimide tube 50.

In FIGS. 2a-2d, various intermediate stages that are run through when a second method according to the invention is carried out are represented. In FIG. 2e, the second arrangement 2 that can be produced by the method according to the invention is depicted.

Figure 2A:
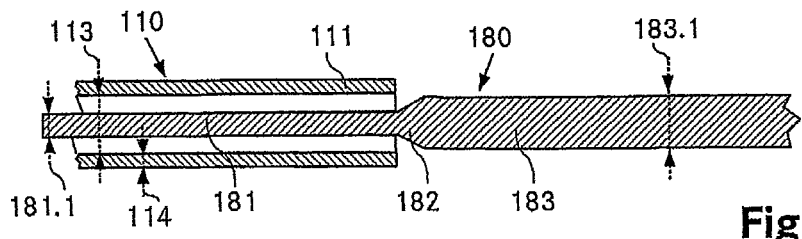
FIG. 2a shows a longitudinal section through a cylindrical piece of wire protruding into the first plastic tube.

In FIG. 2a, an end region 111 of a first cylindrical plastic tube 110 is depicted in longitudinal section on the left-hand side. The first plastic tube 110 has an inside diameter 113 of, for example, 0.7 mm with a wall thickness 114 of, for example, 0.1 mm and consists of polyethylene terephthalate (PET). An end portion 181 of a cylindrical piece of wire 180 protrudes coaxially into the interior of the end region 111. The outside diameter 181.1 of the end portion 181 of the cylindrical piece of wire 180 measures about 0.5 mm, which corresponds to about 71% of the inside diameter 113 of the first plastic tube 110. Outside the first plastic tube 110, the cylindrical piece of wire goes over into a conically widening transitional region 182, which in turn is adjoined by a thickened region 183 of the cylindrical piece of wire 180. The outside diameter 183.1 of the thickened region of the cylindrical piece of wire 180 measures about 0.7 mm and consequently corresponds substantially to the inside diameter 113 of the first plastic tube 110.

Figure 2B:
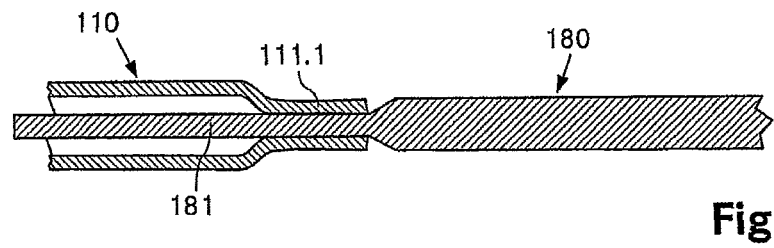
FIG. 2b shows a longitudinal section through the arrangement from FIG. 2a after the end region of the first plastic tube has been formed into a narrowed connecting stub.

FIG. 2b shows the situation after the end region 111 of the first plastic tube 110 has been integrally molded onto the end portion 181 of the cylindrical piece of wire 180 and thereby formed into a connecting stub 111.1. The inside diameter of the connecting stub 111.1 in this way corresponds to the outside diameter of the end portion 181 of the cylindrical piece of wire 180 and has a narrowed outside diameter and a narrowed inside diameter in comparison with the other regions of the first plastic tube 110.

Figure 2C:
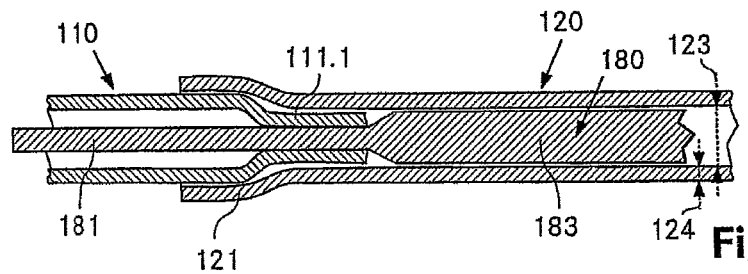
FIG. 2c shows a longitudinal section through the arrangement from FIG. 2b, a second plastic tube additionally having being pushed over the cylindrical piece of wire and the connecting stub.

FIG. 2c shows the situation after a second plastic tube 120 has been pushed coaxially over the thickened region 183 of the cylindrical piece of wire 180 and the connecting stub 111.1 of the first plastic tube 110. The second plastic tube 120 is likewise cylindrical, consists, for example, of nylon and has an inside diameter 123 of, for example, 0.7 mm with a wall thickness 124 of, for example, 0.1 mm. An end region 121 of the second plastic tube thereby protrudes in the longitudinal direction beyond the connecting stub 111.1 of the first plastic tube 110 and lies behind the connecting stub 111.1 on a non-narrowed region of the first plastic tube 110. The end region 121 of the first plastic tube 120 is in this case widened slightly in the radial direction.

A modulus of elasticity of the second plastic tube 120 is in this case less than a modulus of elasticity of the first plastic tube 110.

Figure 2D:
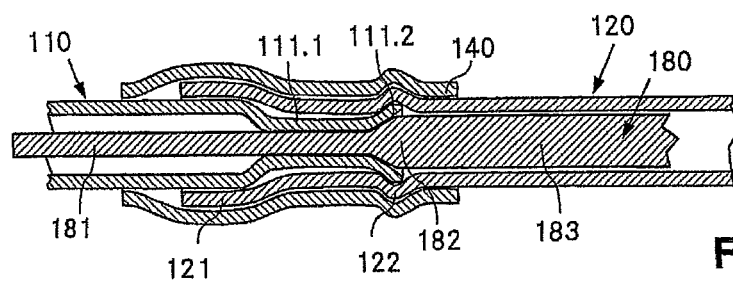
FIG. 2d shows a longitudinal section through the arrangement from FIG. 2c once a free end of the connecting stub has been widened by a thickened region of the cylindrical piece of wire and a shrink-fit tube has been arranged around the connected joint.
Figure 2E:
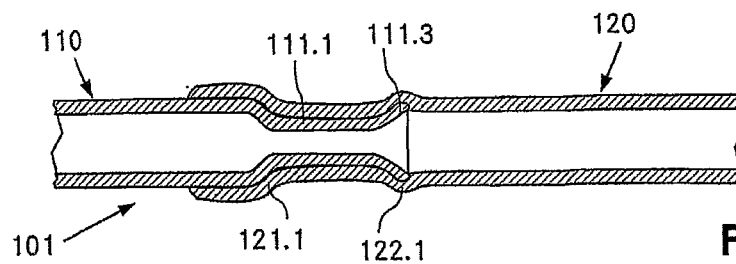
FIG. 2e shows a longitudinal section through the arrangement from FIG. 2d after the forming process and removal of the shrink-fit tube.

FIG. 2d shows the situation after the cylindrical piece of wire 180 has been pushed in the longitudinal direction partially into the formed end region 111.1 of the first plastic tube 110. The conical transitional region 182 of the cylindrical piece of wire 180 is in this case in a region of a free end 111.2 of the connecting stub 111.1. As a result, the free end 111.2 of the connecting stub 111.1 is in a state in which it is substantially conically widened and pressed from the inside against the surrounding second plastic tube 120.

In the region of the widened free end 111.2 of the first plastic tube 110 that is surrounded by the second plastic tube 120, the second plastic tube 120 has a bulged region 122, in which the widened end 111.2 of the first plastic tube 110 engages.

Loosely arranged outside the two plastic tubes 110, 120 is a shrink-fit tube 140, which completely surrounds an overlapping region of the two plastic tubes.

In FIG. 2e, a second arrangement 101 according to the invention, comprising the two plastic tubes 110, 120, is represented after the forming process. The shrink-fit tube 140 represented in FIG. 2c and the cylindrical piece of wire have been removed after the forming process. On account of the forming process, on the connecting stub 111.1 there is a free end 111.3 that has undergone forming and is dimensionally stable.

The end region of the second plastic tube 120 now takes the form of an end region 121.1 that has undergone forming and has been integrally molded from the outside in a forward region onto the connecting stub 111.1 of the first plastic tube 110 and behind the connecting stub 111.1 onto the first plastic tube 110. Further toward the rear, the second plastic tube 120 has a region 122.1 that has undergone forming by bulging and has been integrally molded from the outside onto the widened and formed free end 111.3 of the first plastic tube 110.

In this way, between the connecting stub 111.1 of the first plastic tube 110 and the second plastic tube there is an adhesive and at the same time positive connection that withstands high tensile loads.

Figure 4:
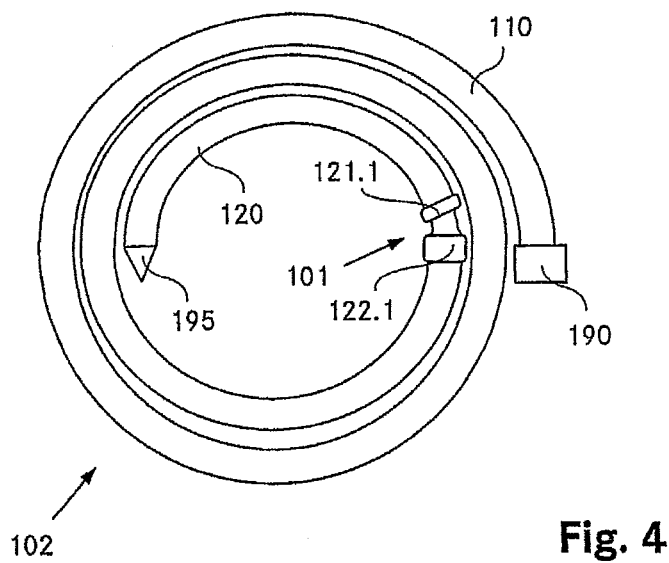
FIG. 4 shows a medical catheter formed into a dimensionally stable spiral and comprising the arrangement from FIG. 2e.

The second arrangement 102 is, for example, a component part of a medical catheter 102, which is represented in FIG. 4.

Figure 3:
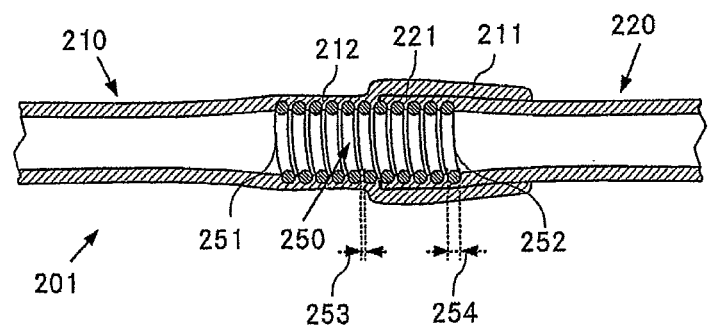
FIG. 3 shows a longitudinal section through a variant of FIG. 1d, a helical spring being arranged as the tubular connecting piece.

FIG. 3 shows a third arrangement 201 according to the invention, which has been produced substantially like the first arrangement 1 and is, for example, a component part of a medical catheter. Instead of the polyimide tube 50 that is present in the first arrangement 1, however, a helical spring 250 has been used in the case of the third arrangement 201 as a tubular connecting piece for connecting a first plastic tube 210 and a second plastic tube 220.

The helical spring 250 consists, for example, of stainless steel wire with a wire diameter 254 of, for example, 0.1 mm. The inside diameter of the helical spring is constant over the entire length and measures, for example, about 0.7 mm, while the individual turns of the helical spring 250 have a spacing 253 of, for example, 0.03 mm. Altogether, the helical spring 250 has ten turns.

The first plastic tube 210 is cylindrical and has an inside diameter of, for example, 0.7 mm with a wall thickness of, for example, 0.1 mm and consists of polyethylene terephthalate (PET). The second plastic tube 20 is likewise cylindrical, consists, for example, of nylon and has an inside diameter 23 of, for example, 0.7 mm with a wall thickness 24 of, for example, 0.1 mm. A modulus of elasticity of the second plastic tube 220 is in this case less than a modulus of elasticity of the first plastic tube 210.

A rear region 212 of the first plastic tube, lying behind an end region 211 of the first plastic tube 210, has in this case been integrally molded coaxially from the outside onto a region of the first end 251 of the helical spring 250 or onto six first turns of the helical spring 250. An end region 221 of the second plastic tube 220 has likewise been integrally molded coaxially from the outside onto a region of the second end 252 of the helical, spring 250 or onto the four remaining turns of the helical spring 250. On account of the integral molding, the helical spring 250 is partially embedded both in the first plastic tube 210 and the second plastic tube 220, the helical spring 250 being let into the two plastic tubes 210, 220 to about a depth of half the wire diameter 254 of the helical spring 250. In this way there is both an adhesive and a positive connection between the two plastic tubes 210, 220 and the helical spring 250.

The end region 211 of the first plastic tube 210, which adjoins the rear region 212 of the first plastic tube in a step-like manner, has also been integrally molded from the outside onto the end region 221 of the second plastic tube 220 and adhesively connected to it.

The helical spring 250 guarantees great bending flexibility, in particular with respect to a longitudinal direction of the third arrangement 201 according to the invention, but at the same time the third arrangement 201 has high tensile strength.

The third arrangement 102 is therefore particularly suitable in the region of the forwardmost 30 cm of a catheter, since this region of the catheter must have great bending flexibility.

FIG. 4 shows a medical catheter 102, which comprises the second arrangement 101 from FIG. 2e. On the right-hand side in FIG. 4 there is a connecting stub 190 of the medical catheter 102, which opens out into the first plastic tube 110. The two connected plastic tubes 110, 120, which form the second arrangement 102 shown in detail in FIG. 2e, in this case take the form of a spiral that has undergone forming and is dimensionally stable, formed by a prior heat treatment at 50° C. Also arranged on the second plastic tube 120 in a known way is a catheter tip 195.

The intermediate stages represented in FIGS. 1c and 2d are subjected to a forming process. For this, shrink-fit tubes 40, 140 from FIGS. 1c and 2d are blown on, for example with hot air. It is important in this case that the plastic tubes that are to undergo forming have been heated up sufficiently, so that at least incipient melting of the plastic tubes occurs. The process parameters required for this, such as the temperature and duration of the blowing on, depend on the one hand on the material of the plastic tubes that are used and on the other hand on the hot air source that is used. Optimum process parameters can be simply determined, for example, in the course of tests.

The previous embodiments should be understood merely as illustrative examples that can be modified as desired within the scope of the invention.

For instance, instead of a polyimide tube 50 with flanges 51, 52, a polyimide tube that is unstructured on the outer side and without flanges can also be used.

In this case, an adhesive connection is substantially formed between the plastic tube and the polyimide tube. It is also possible to use a polyimide tube that has an external thread and/or grooves or to use a tube made of another material that has high strength and dimensional stability even at relatively high temperatures.

It is similarly possible, for example, to use instead of the polyimide tube a tube of a plastic that is reinforced with a wire coil and/or fibrous materials.

It is also conceivable in principle to dispense with the provision of shrink-fit tubes 40, 140 and, for example, instead to carry out the forming process with a press.

It is also conceivable for the tubular connecting piece or the polyimide tube 50 and/or the helical spring 250 to have regions with different inside and/or outside diameters.

This may be expedient in particular whenever plastic tubes with different inside and/or outside diameters are to be connected to one another by the method according to the invention.

The method illustrated in FIGS. 1a-1d may also be carried out moreover without an inner tube 30. The inside diameter of the polyimide tube 50 may in this case also be smaller or greater than the inside diameter of the plastic tubes. Similarly, the helical spring 250 from FIG. 3 may have a smaller or greater inside diameter than the plastic tubes.

The cylindrical piece of wire 180 from FIG. 2a may, for example, also have instead of the conically widening transitional region 182 a differently formed transitional region, which, for example, is formed in a substantially step-like manner. Also conceivable is the use of a cylindrical piece of wire of which the end portion is of a completely conically form.

In the case of the medical catheter 102 depicted in FIG. 4, it is also possible that there are more than two plastic tubes connected to one another. Instead of or in addition to the arrangement 101, the medical catheter 102 may, for example, also include further connections between plastic tubes. This can be produced, for example, by the methods illustrated in FIGS. 1a-1d and in FIGS. 2a-2e. In particular in the region of the tip, the connection of the plastic tubes by a helical spring, as represented for example in FIG. 3, is advantageous, since this type of connection is particularly distinguished by great bending flexibility.

In principle, it is also possible with the method according to the invention to fasten balloons, which may, for example, take the form of tubular elements made of plastic, to a catheter shaft. In this way, the method according to the invention is also suitable in the case of the production of balloon catheters.

To sum up, it can be stated that the invention provides a particularly flexible method that makes it possible to obtain a secure and high-quality connection between thin plastic tubes with extremely small dimensions of a wide variety of materials. At the same time it is possible in particular to dispense with adhesives and with the welding processes offering limited choice of materials. The arrangements or connections produced according the invention from the two plastic tubes have extremely high mechanical strength, so that in particular they even withstand high tensile loads. The method according to the invention can be used particularly advantageously in the production of catheters.

The invention claimed is:

1. A method for coaxially connecting a first plastic tube of a medical catheter to a second plastic tube of said medical catheter comprising the steps of:
   a) plastically deforming an end region of the first plastic tube into a connecting stub having a length, wherein the first plastic tube is plastically deformed such that an outside diameter of the connecting stub is substantially narrowed in comparison with an outside diameter of the first plastic tube while a thickness of the first plastic tube remains constant, said plastic deformation comprising the steps of inserting an end portion of a cylindrical piece of wire into the end region of the first plastic tube and integrally moulding said end region of said first plastic tube onto the end portion of the cylindrical piece of wire to produce the connecting stub;
   b) widening a free end of the connecting stub by pushing a thickened region of the cylindrical piece of wire that adjoins the end portion of the cylindrical piece of wire into the free end of the connecting stub in a direction toward the first plastic tube, wherein an outside diameter of the thickened region corresponds to an inside diameter of the first plastic tube;
   c) pushing the second plastic tube coaxially over the connecting stub, at least over the length of said connecting stub; and
   d) forming at least one of an adhesive and a positive connection in a forming process.

2. The method as claimed in claim 1, wherein during said step of inserting, an outside diameter of the end portion of the cylindrical piece of wire measures 60-80% of an inside diameter of the first plastic tube.

3. The method as claimed in claim 1, wherein, during the forming process, the second plastic tube is integrally molded onto the connecting stub, the connecting stub being widened at the end, thereby forming a positive connection.

4. The method as claimed in claim 1, wherein, during the forming process:
   a) the end portion of the cylindrical piece of wire remains in the connecting stub; and
   b) at least one of the widened transitional region and the thickened region of the cylindrical piece of wire remains in the widened free end of the connecting stub.

5. The method as claimed in claim 1, wherein at least one of the first and the second plastic tube are spirally wound up after the forming process and formed into a dimensionally stable spiral under the application of heat.

6. The method as claimed in claim 1, further comprising the steps of:
   a) softening the second plastic tube during the forming process by a heat treatment;
   b) integrally molding the second plastic tube onto the connecting stub by a pressing force acting in a radial direction.

7. The method as claimed in claim 1, wherein to widen the free end of the connecting stub, pushing a widened transitional region of the cylindrical piece of wire located between said end portion of the cylindrical piece of wire and said thickened region of said cylindrical piece of wire into the free end of the connecting stub in a direction toward the first plastic tube.

8. A method for coaxially connecting a first plastic tube of a medical catheter to a second plastic tube of said medical catheter comprising the steps of:
   a) plastically deforming an end region of the first plastic tube into a connecting stub having a length, wherein the first plastic tube is plastically deformed such that an outside diameter of the connecting stub is substantially narrowed in comparison with an outside diameter of the first plastic tube while a thickness of the first plastic tube remains constant, said plastic deformation comprising steps of inserting an end portion of a cylindrical piece of wire into the end region of the first plastic tube and integrally moulding said end region of said first plastic tube onto the end portion of the cylindrical piece of wire to produce the connecting stub;
   b) pushing the second plastic tube coaxially over the connecting stub, at least over the length of said connecting stub;
   c) widening a free end of the connecting stub by pushing a thickened region of the cylindrical piece of wire that adjoins the end portion of the cylindrical piece of wire into the free end of the connecting stub in a direction toward the first plastic tube, said thickened region having an outside diameter corresponding substantially to an inside diameter of the first plastic tube; and d) forming at least one of an adhesive and a positive connection in a forming process.

\* \* \* \* \*